(12) United States Patent
Rahman et al.

(10) Patent No.: US 11,042,447 B2
(45) Date of Patent: Jun. 22, 2021

(54) RETENTION RULE COMPLIANCE OF RECORD DELETION BASED ON DELETION LOG

(71) Applicant: International Business Machines Corporation, Armonk, NY (US)

(72) Inventors: Sharif Tarequr Rahman, Irvine, CA (US); Long Wang, Chappaqua, NY (US); Anca Sailer, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/586,238

(22) Filed: Sep. 27, 2019

(65) Prior Publication Data

US 2021/0096957 A1 Apr. 1, 2021

(51) Int. Cl.
*G06F 11/14* (2006.01)
*G16H 10/60* (2018.01)

(52) U.S. Cl.
CPC ...... *G06F 11/1451* (2013.01); *G06F 11/1458* (2013.01); *G06F 11/1471* (2013.01); *G16H 10/60* (2018.01)

(58) Field of Classification Search
CPC ............. G06F 11/1451; G06F 11/1471; G06F 11/1458; G16H 10/60
USPC ................ 707/662, 694, 803, 665, 674, 692
See application file for complete search history.

(56) References Cited

U.S. PATENT DOCUMENTS

| 8,392,677 | B2 | 3/2013 | Bunte | |
|---|---|---|---|---|
| 8,745,523 | B2 | 6/2014 | McInerney | |
| 10,133,639 | B2 | 11/2018 | Akbulut | |
| 2007/0271316 | A1 | 11/2007 | Hollebeek | |
| 2009/0125570 | A1 | 5/2009 | Bailey | |
| 2014/0358868 | A1* | 12/2014 | Costecalde | G06F 16/215 707/692 |
| 2015/0127607 | A1* | 5/2015 | Savage | G06F 16/178 707/610 |
| 2017/0053014 | A1* | 2/2017 | Lavallee | G06F 16/93 |
| 2018/0329940 | A1* | 11/2018 | Tiku | G06F 16/21 |

(Continued)

OTHER PUBLICATIONS

Ekblaw et al., "MedRec: Medical Data Management on the Blockchain." Viral Communications, Apr. 11, 2016, 9 pps., <.https://viral.media.mit.edu/pub/medrec>.
Fontes., "Web system for workflow optimization in radiology service", MS thesis, Universidade de Aveiro, 2016, 105 pps.

(Continued)

*Primary Examiner* — Hong C Kim
(74) *Attorney, Agent, or Firm* — Daniel R. Simek (57) ABSTRACT

One or more processors scan to identify component resources of a record retention system and determine relationships among the component resources and data stored on the component resources. Rules corresponding to retention of record data stored on the component resources are received, and a deletion action is determined in response to receiving a request by a user for deletion of record data from the record retention system and the rules corresponding to the retention of data. The one or more processors perform the deletion action on the user's record data associated with the request and compliant with the rules corresponding to the retention of the data among the component resources of the record retention system, and the one or more processors record the deletion action and information associated with the deletion action in a deletion log of the record retention system.

20 Claims, 5 Drawing Sheets

(56) References Cited

U.S. PATENT DOCUMENTS

2019/0272335 A1* 9/2019 Liu .................... G06F 16/125
2019/0333612 A1* 10/2019 Brown ................ G06N 5/045

OTHER PUBLICATIONS

Gilbert et al., "Brewer's Conjecture and the Feasibility of Consistent, Available, Partition-Tolerant Web Services", printed from the Internet on Feb. 28, 2019, 12 pps., <http://www.glassbeam.com/sites/all/themes/glassbeam/images/blog/10.1.1.67.6951.pdf>.

Goldman et al., "Enabling Medical Device Interoperability for the Integrated Clinical Environment". Massachusetts General Hospital Boston United States, Dec. 2016, 97 pps.

Ports et al., "Transactional Consistency and Automatic Management in an Application Data Cache", Dec. 9, 2011, 48 pps., <https://researcher.watson.ibm.com/researcher/files/us-akement/DanPorts.pdf>.

Kevin, "Healthcare in the Digital Age—The Future of Health Records", Victoria University of Wellington, 2017 School of Design, 77 pps.

* cited by examiner

RETENTION RULE COMPLIANCE OF RECORD DELETION BASED ON DELETION LOG

FIELD OF THE INVENTION

The present invention relates generally to the field of data retention, and more particularly to deletion of data records in compliance with data retention system rules.

BACKGROUND OF THE INVENTION

In some areas of data retention, requirements exist for data record to be retained for a specified minimum period of time. The requirements may be supported by business practice, accounting principle, or legal mandate. Data storage has migrated from private data storage devices to cloud environments that include multiple storage devices connected across various locations. Users exercising a "right to be forgotten" in data records are interested in removal or disconnecting identifying attributes from data stored in retention resources.

SUMMARY

Embodiments of the present invention disclose a method, computer program product, and computer system for processing record deletion requests within a record retention system of a distributed cloud environment. The method provides for one or more processors to identify component resources of a record retention system by performing a scan of the system and determining a relationship among the component resources and data stored on the component resources. The one or more processors receive rules corresponding to retention of record data stored on the component resources of the record retention system. The one or more processors, responsive to receiving a request to delete a user's record data from the record retention system, determine a deletion action based on the request to delete the user's record data and the rules corresponding to the retention of data on the record retention system. The one or more processors perform the deletion action on the user's record data associated with the request and compliant with the rules corresponding to the retention of the data among the component resources of the record retention system, and the one or more processors record the deletion action and information associated with the deletion action in a deletion log of the record retention system.

DETAILED DESCRIPTION

Embodiments of the present invention recognize that data retention practices may involve various retention requirements, based on the type of data, the source of data, the location of the data, and the governing body administering the data. Retention requirements may designate a duration in which the data is available for audit or reference. Embodiments also recognize the user's rights and concerns regarding the existence and availability of data about or directed to the user, and the user's desire for deletion of the data, enabling a user's right to be forgotten.

Embodiments of the present invention provide a method, computer program product, and computer system for compliant deletion of data associated with a user, based on retention system rules that include identification of resources within the system that include data, the type of data, the location of the resources, and the inter-relationship of the resources within the system. Embodiments perform deletion actions that result from analysis of user deletion requests, retention system resources, and retention system rules. Embodiments enable routine backup restoration with inclusion of deletions.

In some embodiments of the present invention, a "soft delete" is performed on data designated for deletion, whereas in other embodiments, a "hard delete" is performed, removing the data from designated retention system resources. In some embodiments a deletion log is generated and maintained, recording deletion requests performed and including detail information regarding the deletion, such as a timestamp of the deletion, the data type deleted, and audit records related to the deletion. In some embodiments of the present invention, the rules of the retention system are referenced from an accessible immutable source, such as a blockchain structure operating on a network accessible device. In other embodiments, the retention system includes rules located on other immutable sources.

In some embodiments of the present invention, compliant deletions are performed on one or a combination of: live data sources, which can be queried and are maintained in real-time or near real-time; backup sources used to restore or correct issues associated with the live data source; and archive sources which are often removed from the live data source, kept for retention period requirements, and not readily accessible for data queries. In some embodiments, the deletion action is a "soft delete" in which the user-identifiable information in data records is marked "delete" such that the data records are excluded from data query and viewing but are not physically removed.

In other embodiments, data deletion actions include removal of the requested data records from one or combinations of the live, backup, and archive sources, compliant with the retention system rules. In some embodiments, the deletion action and associated information are added to a deletion log and the deletion information is included in audit log data of system transactions. In some embodiments of the present invention, the deletion action is a modification of user data, replacing new data for previously existing data, such as a change of address, contact information, account information, or other data. Embodiments of the present invention may be applied to a variety of data retention environments, such as, but not limited to, financial records, purchase/procurement records, membership or subscription accounts, and medical records. For simplicity, embodiments are described, herein, referencing medical records as a retention environment.

Figure 1:
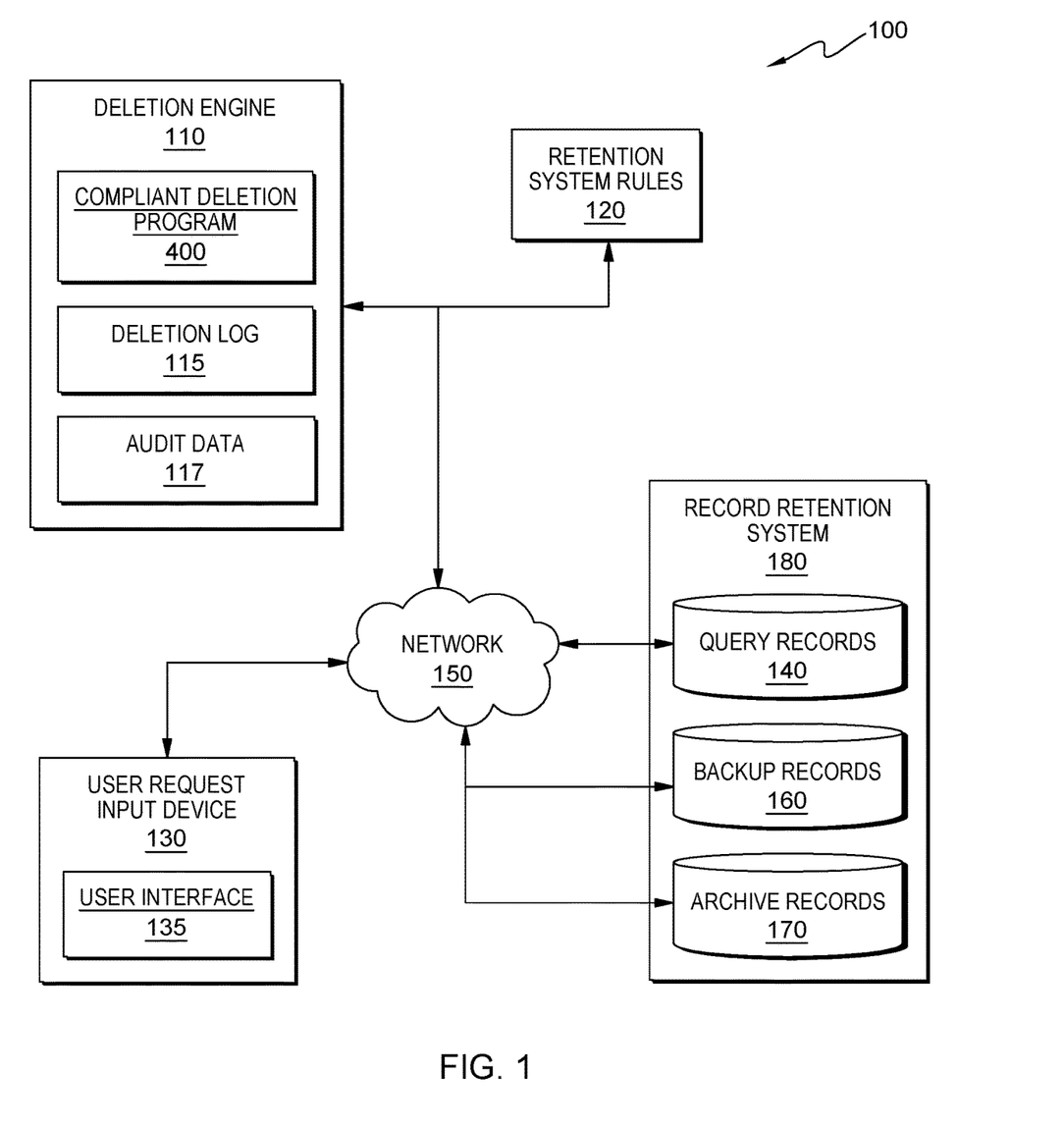
FIG. 1 is a functional block diagram illustrating a distributed data processing environment, in accordance with an embodiment of the present invention.

The present invention will now be described in detail with reference to the Figures. FIG. 1 is a functional block diagram illustrating a distributed data processing environment, generally designated 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes deletion engine 110, retention system rules 120, user request input device 130, and record retention system 180, which includes query records 140, backup records 160 and archive records 170, all connected via network 150.

Network 150 can be, for example, a local area network (LAN), a telecommunications network, a wide area network (WAN), such as the Internet, a virtual local area network (VLAN), or any combination that can include wired, wireless, or optical connections. In general, network 150 can be any combination of connections and protocols that will support communications between deletion engine 110, user request input device 130, retention system rules 120, compliant deletion program 400 operating on deletion engine 110, query records 140, backup records 160, and archive records 170, in accordance with embodiments of the present invention.

Deletion engine 110 is a computing device and includes compliant deletion program 400, deletion log 115, and audit data 117. Deletion engine 110 can be a server computer, a blade computer, a laptop computer, a tablet computer, a netbook computer, or any other programmable electronic computing device capable of receiving, sending, and processing data. Deletion engine 110 is also configured to communicate via network 150 with user request input device 130, retention system rules 120, and authorized to access query records 140, backup records 160, archive records 170, and other computing devices (not shown) within distributed data processing environment 100 via network 150. In other embodiments, deletion engine 110 can represent a virtual computing device operating based on multiple computers as a server system, such as in a cloud computing environment. In another embodiment, deletion engine 110 represents a computing system utilizing clustered computers and components (e.g., database server computers, application server computers, etc.) that act as a single pool of seamless resources when accessed within distributed data processing environment 100. Deletion engine 110 may include internal and external hardware components, as depicted and described in FIG. 5.

Compliant deletion program 400 operates on deletion engine 110 and performs deletion actions based on user requests from user request input device 130 and retention system rules 120. Compliant deletion program 400 determines the identity, location, and relationship of resources, as well as the data type of records comprising record retention system 180. In some embodiments, the resources of record retention system 180 may be distributed across multiple locations and devices. The resource and data type information of stored records are used in generating rules for data retention for the record retention system. In some embodiments the generation of rules includes involvement by an administering user, and once established, the rules are included in an immutable device accessible by deletion engine 110 and compliant deletion program 400. In some embodiments, the immutable device is one or more computing devices that hosts a blockchain structure.

Compliant deletion program 400 receives a request from a user that includes options to delete records from a record retention system. In some embodiments, the request option is for deletion of records from the live data retention system, such as query records 140, which is actively maintained and accessible for record information query, and no deletion of records in backup or archive records. In other embodiments, the user request options include deletion from the live data retention system (query records 140) and backup records 160, and in still other embodiments, the user request option includes combinations of deletion of the user's records from query records 140, backup records 160, and archive records 170, and include deletion of user related information in audit data and recording of deletion actions in deletion log 115. Compliant deletion program 400 reads the rules from the retention system rules 120 and performs a deletion action according to the rules and in light of the user request.

In some embodiments, the deletion action performed is a "soft delete" in which the target records are marked with a "delete" designation, omitting the record from view or query results. In other embodiments the deletion action deletes the records by removing the user identification associated with the user records from all resources of the retention system, for example, removing all patient identification information from medical records of a user. In yet other embodiments, all user related records are removed, but the audit data associated with the user remains. In yet other embodiments, the requested user records are removed from the query records and archive records but remain in the backup records. In some embodiments compliant deletion program 400 analyzes the user deletion request and the retention system rules to determine the compliant deletion action to perform. In some embodiments, the deletion action is a modification of data of existing records.

In some embodiments of the present invention, a restoration action is performed to correct errors or issues discovered in the live data component of the retention system. In embodiments in which soft deletes are performed, the restoration from an appropriate backup is applied to a generated copy of the live data. A copy of a most-recent live data backup is generated, and the soft delete markings included in the most-recent live data backup are applied to the restored live data copy and the transactions recorded in audit data 117. The restored and deletion-updated copy of the live data is then installed as the retention system live data.

In some embodiments in which a restoration action is performed a copy of the live data is generated and the restoration of an appropriately dated backup of the live data is applied to the copy of the live data. Deletions recorded in deletion log 115 are applied to the live data copy to include all deletions performed subsequent to the live data backup applied, and deletion information, such as data type deleted, timestamp of deletion, related records, and other information included in deletion log 115 are included in the audit data 117. In some embodiments, deletions are performed on archive records 170 of record retention system 180. In some embodiments, retention system rules 120 includes record compliance requiring retaining of original records in archive records 170. Embodiments of the present invention provide for compliance of original record retention of archive records and user deletion requests by applying deletions from deletion log 115 to a copy of records from archive records 170. User records designated in deletion log 115 are removed from audit reports of archive records, and archive records 170 retains original records. The user records are effectively deleted (from audit reports), but archive records 170 remains compliant with rules requiring retention for designated time periods.

Deletion log 115 includes logging of records of deletion actions performed on resources of record retention system 180. Deletion log 115 includes information regarding the user request, the resources associated with the deletion, timestamp of deletion, the type or extent of deletion, among other information. In some embodiments, deletion log 115 is applied to a copy of a backup record to include deletion actions performed subsequent to a restoration time period, prior to restoring the data of that time period to the main live data source. In some embodiments, deletion log 115 includes information of a deletion action in which one of: a soft delete, a delete of a user's identification, or a full data content delete, are performed against one or a combination of the live data records, the backup records, and the archive records.

Audit Data 117 includes information of transactions performed against the live retention records, such as query records 140, and may also include transactions performed against backup records 160 and archive records 170. Audit data 117 includes data associated with deletion actions and data restoration.

Retention system rules 120 includes requirements for retaining data within the record retention system. The rules provide guidance for deletion engine 110 and compliant deletion program 400. Retention system rules 120 are based on identification of the resources comprising the record retention system, the location of resources to determine location-based compliance, the relationship of resources within the retention system, and the record data type stored on the respective resources, enabling deletion actions that target user identification related information on current live records (query records 140), backup records 160, and archive records 170 resources. In some embodiments of the present invention, retention system rules 120 receives input to rules from an authorized user, such as a system administrator. Embodiments of the present invention perform deletion actions that are compliant with the rules associated with the record retention system and aligned with requests from users.

For example, retention system rules 120 may require retention of records for 5 years. Deletion actions addressing a user request for record deletion may include marking records as "delete", preventing the records from view or query results, but the records are retained with included "deletion" markings. Subsequent to the 5-year retention requirement, records are permanently deleted from all record resources. In other embodiments, the deletion actions may delete the records from query records 140 and backup records 160, but retain the original records present in archive records 170. In yet other embodiments, compliance rules may be met by deletion actions that record the deletion transactions and corresponding information in deletion log 115 and perform deletions of records in query records 140, backup records 160, and retaining records in archive records 170, but deleting records from a copy of archive records 170 used to generate audit reports, by applying deletions designated and stored in deletion log 115.

User request input device 130 is a computing device including user interface 135 that enables a user to submit a request for deletion of records from resources of the record retention system. User interface 135 enables a user to provide input and receive output from user request input device 130. User request input device 130 can be a server computer, a blade computer, a laptop computer, a tablet computer, a netbook computer, a smart phone, a Personal Digital Assistant (PDA), or any other programmable electronic computing device capable of receiving, sending, and processing data, and communicating via network 150 with deletion engine 110, retention system rules 120, and record retention system 180, and other computing devices (not shown) within distributed data processing environment 100 via network 150. In other embodiments, user request input device 130 can represent a virtual computing device operating based on multiple computers as a server system, such as in a cloud computing environment. In another embodiment, user request input device 130 represents a computing system utilizing clustered computers and components (e.g., database server computers, application server computers, etc.) that act as a single pool of seamless resources when accessed within distributed data processing environment 100. User request input device 130 may include internal and external hardware components, as depicted and described in FIG. 5.

Record retention system 180 includes a plurality of storage and processing devices that collectively perform transactions associated with user data. Record retention system 180 stores records according to retention requirements applicable to record retention system 120 and includes a live accessible data record source, such as query records 140, a collection of data backups, such as backup records 160, and archived data such as archived records 170.

An example of record retention system 180 may be a collection of resources storing FHIR (fast health interoperability resources) standard information. One resource device may store files that are designated to include patient-specific information, such as identification, location, and account information. Other resources may be designated for medical services, practitioners, diagnosis, medications, and contacts/guardians. The relationships between the resources may be linked by patient identification, account, practitioner or other data linking key. Deletion actions performed by compliant deletion program 400 includes options which are applied by deletion engine 110 to comply with retention system rules 120. Options may include deletion of identification data and keys linking a user to records, "soft delete" of records by marking selected records as "delete", preventing view or query of the selected records, or removal of records from one or a combination of live, backup, or archive records, and recording the deletion actions in deletion log 115 along with information corresponding to the deletion action.

Query records 140 is a live source of stored data records for record retention system 180. Query records 140 is the primary data source for current user record searches and transactions. In some embodiments of the present invention, query records 140 includes multiple resources storing data and processing transactions, which may be distributed across multiple devices in multiple locations. Query records 140 is the source of record data for record retention system 180, to which a transaction, deletion action, data restore, or query is applied.

Backup records 160 is a collection of one or more storage resources that include backup copies of query records 140. In some embodiments, backup records 160 receives a regularly scheduled backup copy of query records 140. In other embodiments, backup records 160 or a copy of a particular backup record of backup records 160 is applied to a portion of query records 140 in a transaction to restore a particular timeframe of data. In some embodiments, a copy of a backup record is cross-matched with deletion log 115 to include deletion requests by users to the backup record copy prior to restoration of the data record to the live record source, such as query records 140.

Archive records 170 is a collection of one or more storage resources that include archived copies of query records 140. Archive records 170 are not readily accessible by users for queries but are retained for compliance purposes. In some embodiments of the present invention, deletion actions are applied to a copy of data records of archive records 170 to generate audit reports. In accordance to the rules corresponding to the record retention system, deletions designated in deletion log 115 are applied to the copy of records of archive records 170 and the resulting data of the copy of records with deletions is used to generate the audit report. The deletions are included in the audit report and archive records 170 retains the original record data.

Figure 2:
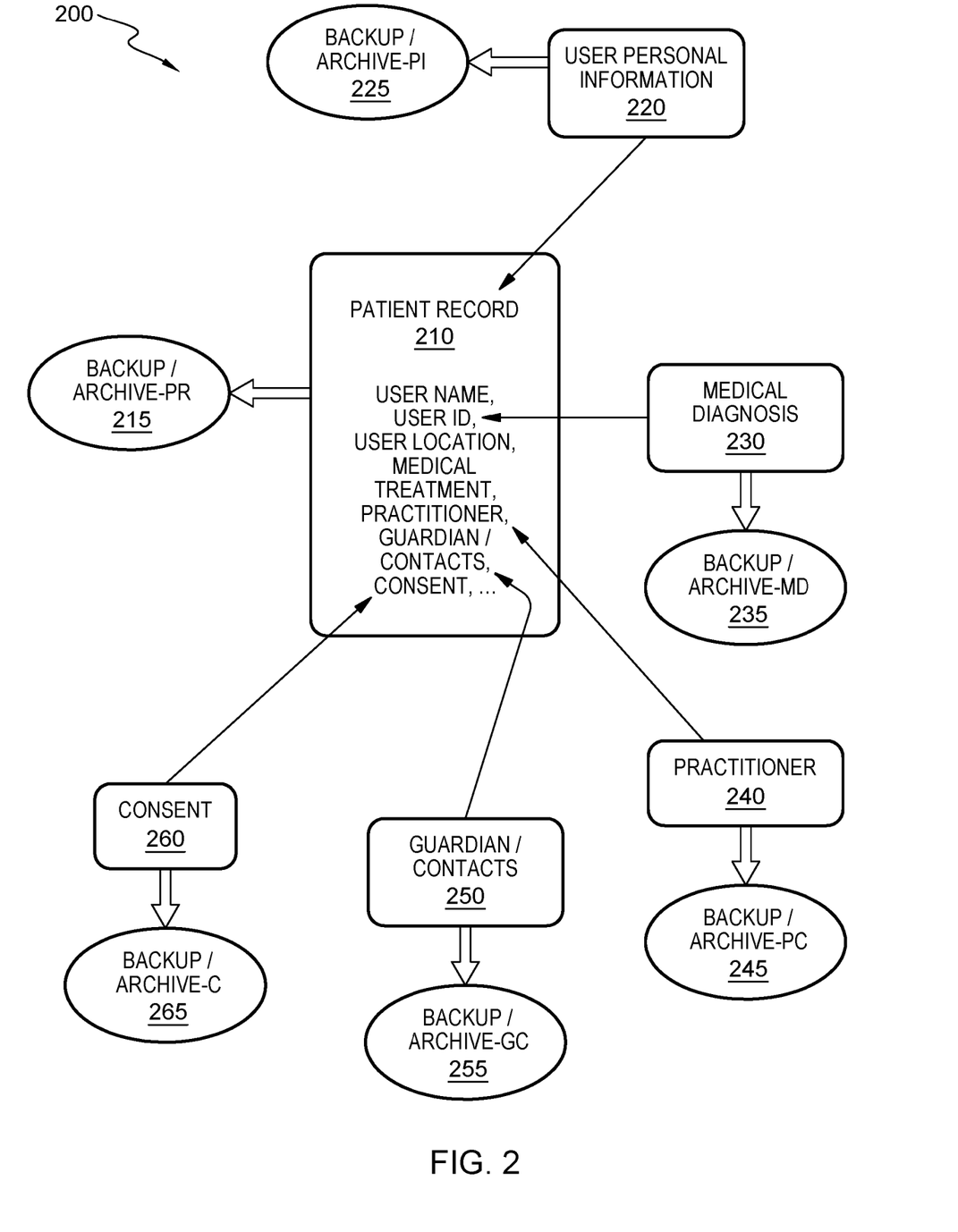
FIG. 2 is a functional block diagram illustrating distributed data retention resources including backup and archive components within the distributed data processing environment of FIG. 1, in accordance with an embodiment of the present invention.

FIG. 2 illustrates component resources of retention system 200 as an example structure of stored record information across multiple resources, within distributed data processing environment 100 of FIG. 1, in accordance with an embodiment of the present invention. FIG. 2 resources include: patient record 210, backup/archive-PR 215, user personal information 220, backup/archive-PI 225, medical diagnosis 230, backup/archive-MD 235, practitioner 240, backup/archive-PC 245, guardian/contacts 250, backup/archives-GC 255, consent 260, and backup/archive-C 265.

The resources of FIG. 2 include exemplary medical record information for patients, such as FHIR (fast health interoperability resources) standard information. Patient record 210 resource enables a view of high-level patient information consolidated from the additional resources of retention system 200. Patient record 210 may include, for example, user name and user identifying information of patients, medical diagnosis and treatments, practitioners administering medical services, guardian and/or contact information of the patient, and consent records for treatment. Patient record 210 receives high-level patient information from user personal information 220, medical diagnosis 230, practitioner 240, guardian/contacts 250 and consent 260 resources of retention system 200. Information of patient record 210 is periodically backed up, and at pre-determined subsequent timeframes archived in backup/archive-PR 215 resource.

User personal information 220 is a retention resource of retention system 200 that includes information identifying or associated with the identity of a patient. User personal information 220 may include patient name, address, identification code, account information, dependent/dependency information, as well as other personal information. User personal information 220 resource generates backup copies of live data at scheduled periods, and at pre-determined timeframes, backup copies are archived in backup/archive-PI 225 resource.

Medical diagnosis 230 is a retention resource of retention system 200 that includes information regarding diagnosis and treatment information of a patient. Medical diagnosis 230 may include all instances of patient medical visits, diagnosis details and treatment records corresponding to respective diagnosis. Live data retained on medical diagnosis 230 resource is backed up at scheduled periods, and at pre-determined timeframes backup copies of medical diagnosis 30 information are archived in backup/archive-MD 235 resource.

Practitioner 240 is a retention resource of retention system 200 that includes information identifying practitioners administering medical service to the patient. Practitioner 240 may include practitioner name, ID, area of practice, medical group affiliation, as well as other practitioner related information. Live data of practitioner 240 resource information is backed up at scheduled periods, and at predetermined timeframes backup copies of practitioner 240 information are archived in backup/archive-PC 245 resource.

Guardian/contacts 250 is a retention resource of retention system 200 that includes information of guardian identification of the patient and/or contact information of other users the patient has identified as a contact and/or a provider of certain information regarding the patient's medical records and care. Guardian/contacts 250 may include name, identification code, relationship, location, and contact information of a patient's guardian, and/or similar information of contacts designated by the patient. Live data resource of guardian/contacts 250 is backed up at scheduled periods, and at predetermined timeframes backup copies of guardian/contacts 250 information are archived in backup/archive-GC 255 resource.

Consent 260 is a retention resource of retention system 200 that includes information identifying practitioners administering medical service to the patient. Consent 260 resource may include information regarding patient consent provided for particular medical testing and treatments. Consent 260 may include a timestamp of consent, scheduling of tests and/or treatments, identification of a practitioner performing the test or treatment, as well as other information. Live data of consent 260 resource is backed up at scheduled periods, and at predetermined timeframes backup copies of consent 260 information are archived in backup/archive-C 265 resource.

In some embodiments of the present invention, a user identified as a patient having records stored in retention system 200 may request deletion of their records. Embodiments of the present invention perform deletion requests based on rules determined and applied to retention system 200 and aligned with the request from the user. In some embodiments, a request for deletion of records includes marking the designated records with a "delete" indicator that omits the records from view or query in the live data retention resources, such as query records 140.

In some embodiments, the record information is retained consistent with the retention rules within retention system 200 by "deletion" indicators marking the records, which may be applied to combinations of live data record resources, and backup record resources to meet retention rules. In some embodiments "deletion" indicator markings are included with user record information to comply with requests for deletion of user data in backup copies and if allowed in compliance rules, in archive records and maintaining compliance with retention rules applicable to retention system 200. In other embodiments, the records requested for deletion are removed from the live data record resources but marked by "deletion" in backup records, maintaining applicable retention rules.

In some embodiments of the present invention a deletion log, such as deletion log 115, in which deletions performed as a result of deletion requests are stored, along with information details associated with deletion transactions. Deletion information details may include, for example, a timestamp of the deletion, the type of record(s) deleted, the resources to which the deletion actions are applied, the type of deletion action, and audit data related to or affected by the deletion. In some embodiments of the present invention, deletions from audit records, such as audit records 170, are performed by applying deletions recorded in deletion log 115 to a copy of records from archive records 170, effectively removing deletions from archive records of the copy, and using the copy to generate audit reports of the archive records. Deletions are included in the audit report, while archive records 170 retains the original records.

Figure 3:
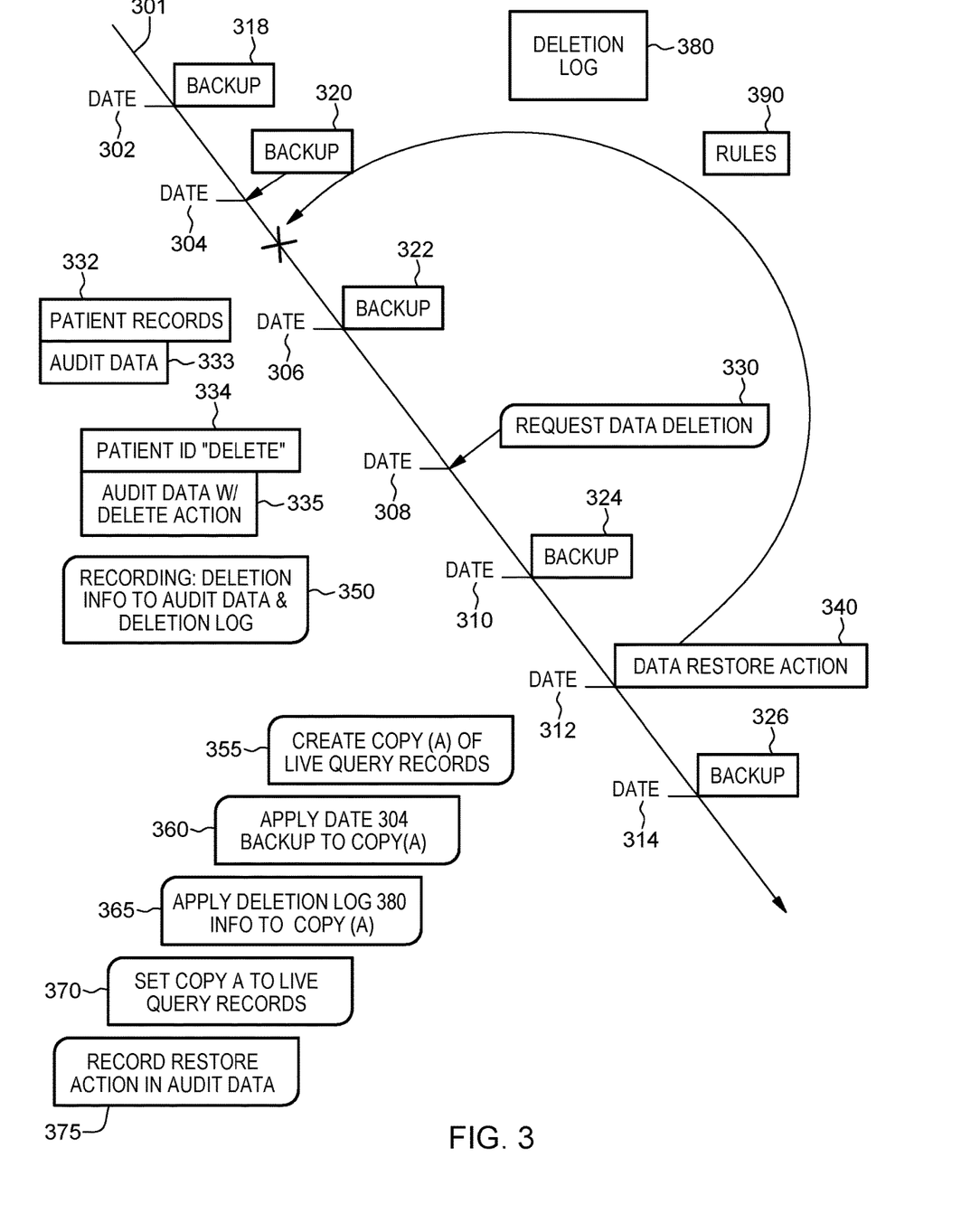
FIG. 3 is a functional block diagram illustrating data restoration subsequent to a compliant deletion action in accordance with an embodiment of the present invention.

FIG. 3 illustrates an example record restoration sequence including a deletion of records requested by a user and applying backup records and deletion log information to correct a discovered data issue, in accordance with an embodiment of the present invention. Timeline 301 depicts an example sequence of activity of a record retention system, such as record retention system 180 (FIG. 1). Timeline 301 includes multiple points-in-time depicted as date 302, date 304, date 306, date 308, date 310, date 312, and date 314 in which date 302 occurs prior to date 304, date 304 occurs prior to date 306, and the time line progresses similarly for the other depicted date points. At dates 302, 304, 306, 310 and 314, backup 318, backup 320, backup 322, backup 324, and backup 326 are generated, respectively, from the live record retention system. Backup 322, performed on date 306 is depicted as including patient records 332 and audit data 333. The patient ID and attributes include information identifying or associated with the identity of the patient. The audit data includes a record of transactions made to the live record retention system.

At date 308, request data deletion 330 is received from a user requesting deletion of the user's record data. The user is a patient and requests deletion of all records associated with the user in the live record retention resource(s) of the record retention system. Compliant deletion program 400 performs the authorized deletion by referencing rules 390 and determining a deletion action compliant with rules 390 and the user's request. For example, compliant deletion program 400 performs a "soft delete" of the user's records by marking the records with a "delete" indicator that excludes the record's data from inclusion in viewing requests or data query results from the live data records resource(s). Patient ID "delete" 334 and audit data w/delete action (335) include the soft delete action of the patient records. Recording 350 includes adding the delete action to audit data 335, and the delete action and related information are added to deletion log 380. The related information may include, but is not limited to: timestamp of deletion, deletion action taken, type of record data deleted, audit records related to the deletion action, and identification of resources from which records are deleted.

In some embodiments of the present invention, the user's patient ID and associated information linking to the identity of the user are marked with the "delete" indicator. In other embodiments, the user's records across other resources, such as backup 322, 320 and 318 of the record retention system are marked with the "delete" indicators. In other embodiments, the requested records to be deleted are marked with the "delete" indicator and are removed from the live record retention system following a subsequent backup of record data that includes the records marked with the "delete" indicator. In some embodiments, consistent with retention rules applicable to the record retention system, at a subsequent time of transferring the backup records to archive records, the "delete" indicators are included in the transfer of the backup records to archive records, and the requested records for deletion are removed from the copy of backup records. In other embodiments in which original records are required to be retained in archive records by rules 390, record data added to archive records includes the original record data, and deletions are performed on a copy of records from the archive by applying deletion data recorded in deletion log 380. In some embodiments, subsequent to archiving of backup records, the backup records may be discarded.

Continuing with the example timeline of FIG. 3, a scheduled backup 324 is performed at date 310. At date 312 an issue (or error) is detected (subsequent to request data deletion 330) in the records between backup dates 304 and 306 and a data restore action 340, is required. The restoration action includes: create copy (A) of live query records 355; apply backup records from date 304 to copy (A) of live records 360; apply deletion log information to copy (A) 365; set copy (A) to replace live query records 370; and record the restore action in audit data 333. In some embodiments in which a soft delete marking is applied to record data, a copy of the most recent backup is generated, and soft delete markings of data records of the most recent backup are applied to the copy (A) of live records 355 to which the restoration of backup records 360 have been applied, and set as the live query records 370.

Figure 4:
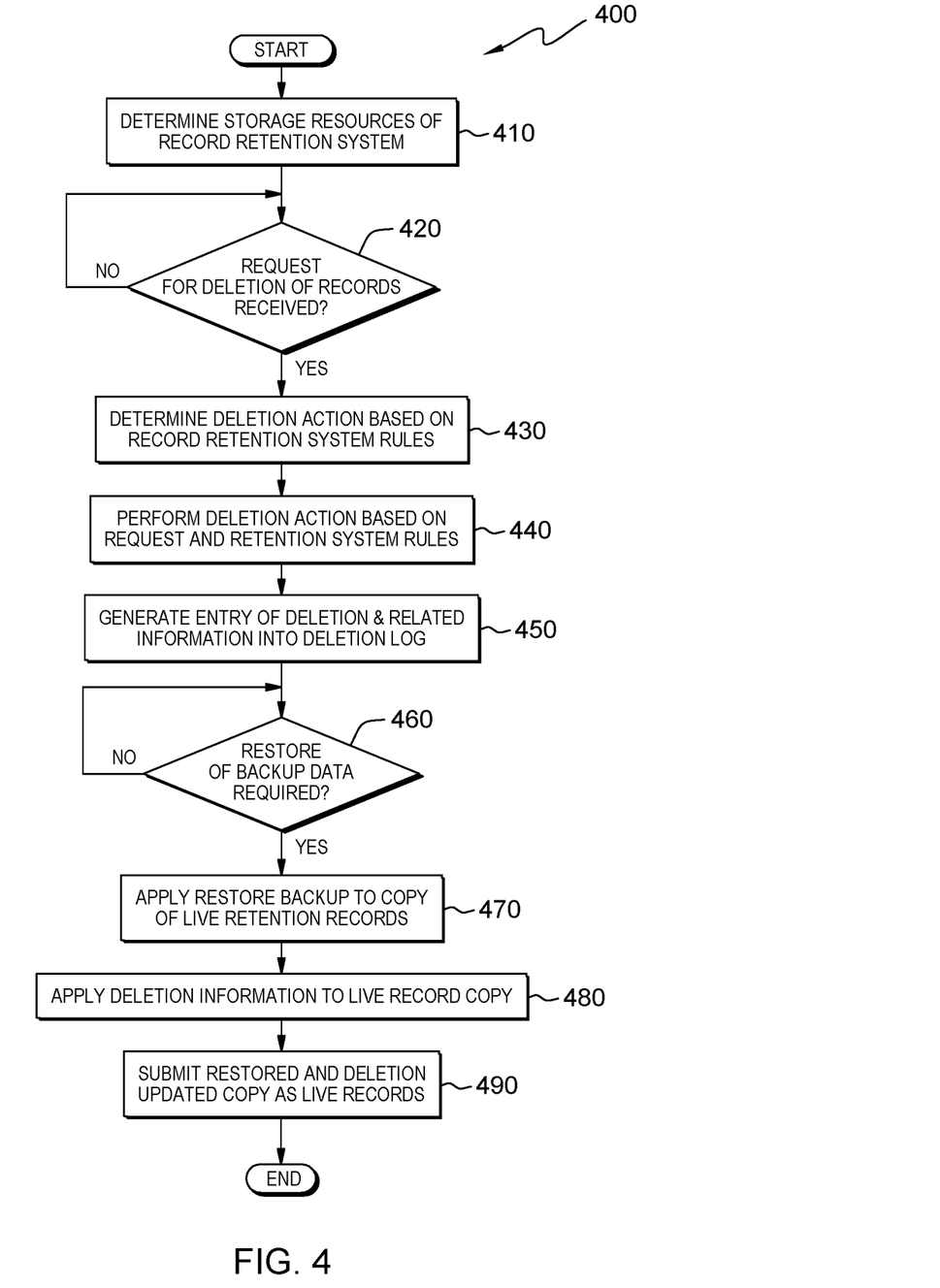
FIG. 4 illustrates operational steps of a compliant deletion program, inserted on a computing device within the distributed data processing environment of FIG. 1, in accordance with an embodiment of the present invention.

FIG. 4 illustrates operational steps of compliant deletion program 400, operating on deletion engine 110 within distributed data processing environment 100 of FIG. 1, in accordance with an embodiment of the present invention. Compliant deletion program 400 performs a scan to determine storage resources of a record retention system (step 410). By performing a scan of the record retention system, compliant deletion program 400 identifies component resources of information storage and determines relationships among data records stored on the component resources. Relationships may include keys linking information within and between tables, files, and user-identifying data. In some embodiments, compliant deletion program 400 determines hardware and software storage components of the record retention system, data types stored within the resources and relationships between the resources, which may include resource location, primary keys, candidate keys, or other identifiers linking storage resources and subcomponents within storage resources.

For example, compliant deletion program 400 scans storage resources of retention system 200 (FIG. 2). Program 400 identifies the resources of retention system 200, which include: user personal information 220 and corresponding backup/archive-PI 225; medical diagnosis 230 and corresponding backup/archive-MD 235; practitioner 240 and corresponding backup/archive-PC 245; guardian/contacts 250 and corresponding backup/archive-GC 255; consent 260 and corresponding backup/archive-C 265; and patient record 210 linked to the scanned resources, and the corresponding backup/archive resource-PR 215. Compliant deletion program 400 determines the relationship between resources and the type of data stored in each resource, such as identification information in user personal information 220 and backup/archive-PI resources.

Having completed and retained information from the scanning of the record retention system, the information is used to generate compliance rules for retention of the data stored in the record retention system. In some embodiments the rules may be generated by one or more users based on local and governing requirements aligned with the storage resource information obtained by the scan performed by compliant deletion program 400. In other embodiments, compliant deletion program 400 is provided local and governing data retention requirements and generates rules for the record retention system. Generating rules may include supervised learning techniques to determine deletion actions that meet retention compliance and user deletion requests. In some embodiments, the generated rules are included in one or more immutable devices, such as blockchain structures, accessible by deletion engine 110, compliant deletion program 400, and authorized administrators.

Compliant deletion program 400 determines whether a request for deletion of records has been received (decision step 420). In some embodiments of the present invention, a request for deletion of records is received from a user regarding the user's data records. In other embodiments, the request may be received by an administrator acting on behalf of one or more users. The request is generated from a computing device, such as user request input device 130 (FIG. 1) and transmitted to compliant deletion program 400, operating on a deletion engine, such as deletion engine 110, via network 150. For the case in which compliant deletion program 400 determines that no request for deletion of records is received (step 420, "NO" branch), compliant deletion program 400 returns into a "listen" state waiting for receipt of a request to delete records.

For the case in which compliant deletion program 400 determines that a request for deletion of records has been received (step 420, "YES" branch), compliant deletion program 400 determines a deletion action based on retention system rules 120 and the received request (step 430). For example, compliant deletion program 400 accesses retention system rules 120, which may include what data, what operations, which resources, and what type of deletion action. Compliant deletion program 400 determines that rules require retention of records in a component of the retention system for at least 5 years.

Compliant deletion program 400 determines a deletion action that meets compliance of retention system rules 120 and deletion of the user's information from viewable and search-access records. Deletions may include, for example: delete from FHIR_Service, where PatientID="patientA", delete from FHIR_Service Backups, where ID="PatientA". Compliant deletion program 400 removes requested records from query records 140 and marks the requested records as "delete" in backup records 160. At a subsequent time in which the deletion requested records in backup records 160 are transferred to archive records 170, the "delete" marks are removed in the transfer, if retention compliance requires original record data in archive records. If original records are not required in archive records for retention requirements, in some embodiments, the "delete" mark in backup records may be transferred with the deletion requested records to archive records 170, and the deletion requested records of backup records 160 are removed. In some embodiments, backup records are deleted subsequent to being transferred to archive records 170.

Having determined a deletion action, compliant deletion program 400 performs the deletion action based on the request and retention system rules (step 440). In some embodiments, compliant deletion program 400 performs a soft delete of requested records in the live records resource and backup records resource. In other embodiments, the requested record deletions are removed from the live record resources and marked as deleted in backup resources until transferred to archive resources. In response to compliance rules to maintain original record data in archive records, the record data marked "delete" in the live or the backup records are removed, and the original record data are included in the transfer of records to the archive records.

Compliant deletion program 400 generates an entry of deletion and related information into the deletion log (step 450). In some embodiments of the present invention, deletion actions are recorded in a deletion log, and information associated with the deletion is included in the deletion log entry. For example, having received a deletion request and completed a deletion action, compliant deletion program 400 enters the deletion action into deletion log 115 (FIG. 1). The entry may include information associated with the deletion action, such as the deletion action being a "soft delete", a timestamp of the deletion action, the resources included in the action, and may include additional information such as the data type and relationship keys between resources involved in the deletion.

Compliant deletion program 400 determines whether a restoration of backup data records is required (decision step 460). A data restoration notification may be received indicating restoration of backup data is required due to data loss, data corruption, or discovery of issues with the retention of data records. For the case in which compliant deletion program 400 determines that no restoration of backup data is required (step 460, "NO" branch), compliant deletion program 400 returns and remains in a "listen" state for a request to perform a restoration of backup data. For the case in which compliant deletion program 400 determines that a restoration of backup data is required (step 460, "YES" branch), compliant deletion program 400 proceeds to step 470 and applies appropriate backup records to a copy of the live retention records (copy (A)). In some embodiments, the appropriate backup records replace the missing, corrupt, or erroneous records in the copy of the live retention records. Deletion actions may not be included in the appropriate backup records to apply or records may have been removed as part of a deletion action performed subsequent to the data record issue requiring restoration.

Compliant deletion program 400 applies deletion action information to the live record copy (step 480). Applying deletion action information recorded in the deletion log, updates the copy of the live retention records to reflect deletion actions that may have affected the historic live retention records and the backup records. For example, (referring to FIG. 3) a requirement for data restore action 340 is determined at date 312. Records of backup 322 are determined to correct the discovered issue. Copy (A) of live retention records is made, such as a copy of query records 140. Backup 322 is applied to copy (A) and the deletion actions of deletion log 380 are applied to copy A to accurately include the recorded deletion actions in the backup-adjusted copy (A). Copy (A) includes backup records correcting data issues and performed deletions.

Compliant deletion program 400 submits the restored and deletion updated copy as the live retention records (step 490). Subsequent to applying the appropriate backup records and deletion action information the copy (copy (A)) of live retention records, replaces the previous live retention records. Having completed the retention record restoration, including deletion action performed, compliant deletion program 400 ends.

Figure 5:
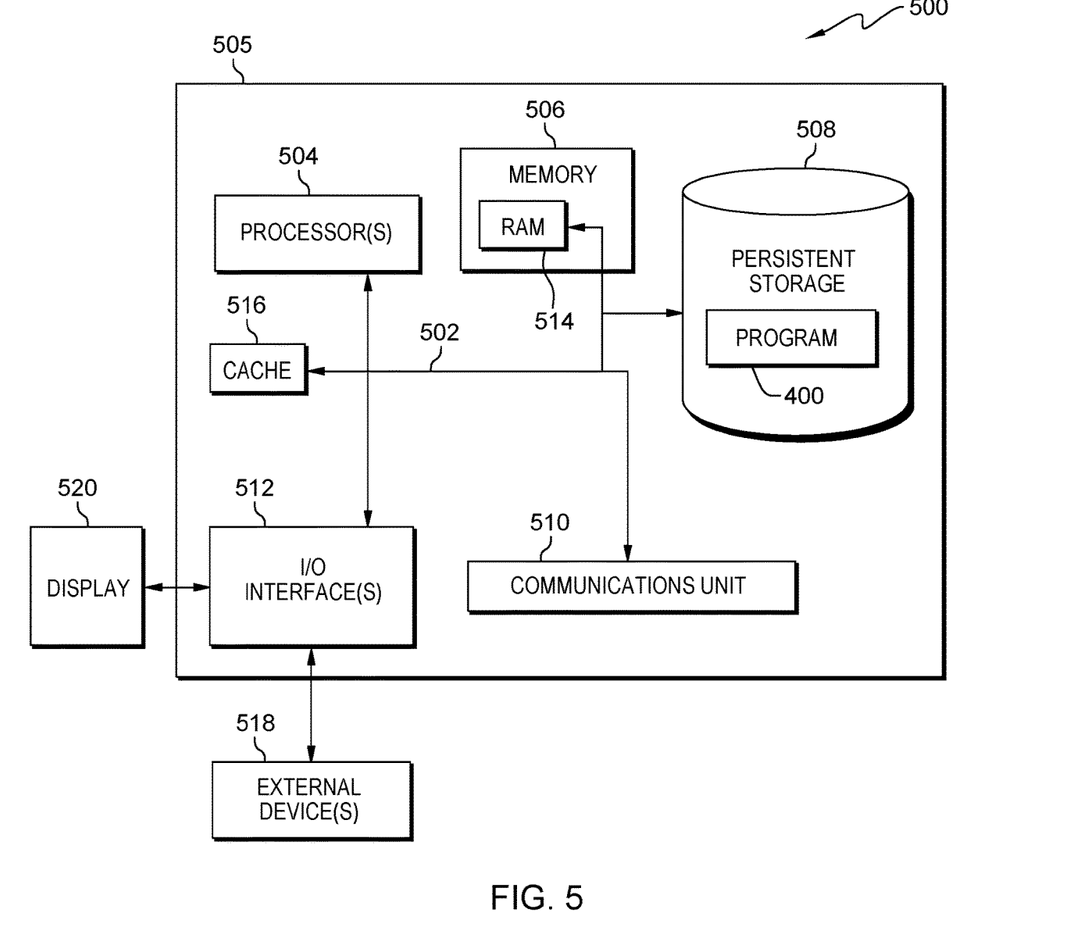
FIG. 5 depicts a block diagram of components of a computing system, including a computing device capable of operationally performing the compliant deletion program of FIG. 4, in accordance with an embodiment of the present invention.

FIG. 5 depicts a block diagram of components of computing system 500, which includes computing device 505. Computing device 505 includes components and functional capability similar to user request input device 130 and deletion engine 110 (FIG. 1), in accordance with an illustrative embodiment of the present invention. It should be appreciated that FIG. 5 provides only an illustration of one implementation and does not imply any limitations regarding the environments in which different embodiments may be implemented. Many modifications to the depicted environment may be made.

Computing device 505 includes communications fabric 502, which provides communications between computer processor(s) 504, memory 506, persistent storage 508, communications unit 510, and input/output (I/O) interface(s) 512. Communications fabric 502 can be implemented with any architecture designed for passing data and/or control information between processors (such as microprocessors, communications and network processors, etc.), system memory, peripheral devices, and any other hardware components within a system. For example, communications fabric 502 can be implemented with one or more buses.

Memory 506, cache memory 516, and persistent storage 508 are computer readable storage media. In this embodiment, memory 506 includes random access memory (RAM) 514. In general, memory 506 can include any suitable volatile or non-volatile computer readable storage media.

Compliant deletion program 400 is stored in persistent storage 508 for execution by one or more of the respective computer processors 504 via one or more memories of memory 506. In this embodiment, persistent storage 508 includes a magnetic hard disk drive. Alternatively, or in addition to a magnetic hard disk drive, persistent storage 508 can include a solid-state hard drive, a semiconductor storage device, read-only memory (ROM), erasable programmable read-only memory (EPROM), flash memory, or any other computer readable storage media that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer readable storage medium that is also part of persistent storage 508.

Communications unit 510, in these examples, provides for communications with other data processing systems or devices, including resources of distributed data processing environment 100. In these examples, communications unit 510 includes one or more network interface cards. Communications unit 510 may provide communications through the use of either or both physical and wireless communications links. Compliant deletion program 400 may be downloaded to persistent storage 508 through communications unit 510.

I/O interface(s) 512 allows for input and output of data with other devices that may be connected to computing system 500. For example, I/O interface 512 may provide a connection to external devices 518 such as a keyboard, keypad, a touch screen, and/or some other suitable input device. External devices 518 can also include portable computer readable storage media such as, for example, thumb drives, portable optical or magnetic disks, and memory cards. Software and data used to practice embodiments of the present invention, e.g., compliant deletion program 400 can be stored on such portable computer readable storage media and can be loaded onto persistent storage 508 via I/O interface(s) 512. I/O interface(s) 512 also connect to a display 520.

Display 520 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for processing record deletion requests within a record retention system of a distributed cloud environment, the method comprising:
   one or more processors identifying component resources of a record retention system by performing a scan of the record retention system;
   the one or more processors determining a relationship among the component resources and data stored on the component resources;
   the one or more processors receiving rules corresponding to retention of record data stored on the component resources of the record retention system;
   the one or more processors responsive to receiving a request to delete a user's record data from the record retention system, determining a deletion action based on the request to delete the user's record data, the relationship among the component resources and the rules corresponding to the retention of data on the record retention system;
   the one or more processors performing the deletion action on the user's record data associated with the request and compliant with the rules corresponding to the retention of the data among the component resources of the record retention system; and
   the one or more processors recording the deletion action and information associated with the deletion action in a deletion log of the record retention system.

2. The method of claim 1, further comprising:
   the one or more processors receiving a notification to perform a restoration of record data of a first timeframe from a backup data component of the component resources of the record retention system associated with the first timeframe;
   the one or more processors generating a copy of a live record data component of the component resources of the record retention system;
   the one or more processors applying backup data from the backup data component associated with the first timeframe to the copy of the live record data component;
   the one or more processors applying the deletion action and the information associated with the deletion action to the copy of the live record data component, based on the deletion log of the record retention system;
   the one or more processors installing the copy of the live record data component of the record retention system as the live record data component of the record retention system; and
   the one or more processors recording the deletion actions in an audit log of the record retention system.

3. The method of claim 1, wherein the rules corresponding to the retention of data stored on the component resources and the deletion actions and information associated with the deletion actions, included in the deletion log, are stored on an immutable device.

4. The method of claim 3, wherein the immutable device is a blockchain structure hosted on a computing device as a component resource of the record retention system.

5. The method of claim 1, wherein the deletion log is a most recent backup of a live record data component of the component resources of the retention system.

6. The method of claim 1, wherein performing the deletion action further comprises:
   the one or more processors applying the deletion action to a copy of an archive record data component of the component resources of the record retention system, based on deletion information of the deletion log; and
   the one or more processors generating a report of the archive record data based on the copy of the archive record data including the applied deletions.

7. The method of claim 1, wherein, the deletion action includes a soft delete by marking the record data requested for deletion by the user with a "delete" label enabling exclusion of the user's record data from view or query results.

8. The method of claim 1, wherein the deletion action removes the record data requested for deletion by the user from the component resources of the record retention system, and maintains compliance of the rules corresponding to retention of record data by retaining the records of the user requested for deletion in at least one resource of the component resources of the record retention system.

9. The method of claim 8, wherein the one resource of the component resources of the record retention system is an archive record resource.

10. The method of claim 1, wherein the user's record data requested for deletion from the component resources are removed from resources of the record retention system by the deletion action, and the deletion action includes storing details of deletions made and information associated with the deletions made, in the deletion log stored on an immutable device.

11. The method of claim 1, further comprising:
one or more processors receiving a notification to perform a restoration of record data of a first timeframe of a live record data component of the record retention system to which soft deletions have been applied as deletion actions, wherein soft deleted record data is excluded from view or query results and the soft deleted record data remains in the respective record data component of the record retention system;
the one or more processors generating a copy of the live record data component of the record retention system;
the one or more processors applying backup data from a backup data component to the copy of the live record data component;
the one or more processors applying instances of the soft deletions from a copy of backup data from the backup data component, generated from a most recent timeframe, to the copy of the live record data component of the record retention system;
the one or more processors installing the copy of the live record data component of the record retention system as the live data component of the record retention system; and
the one or more processors recording the deletion actions in an audit log of the record retention system.

12. A computer program product for processing record deletion requests within a record retention system of a distributed cloud environment, the computer program product comprising:
one or more computer readable storage media and program instructions stored on the one or more computer readable storage media, the program instructions comprising:
program instructions to identify component resources and data of a record retention system by performing a scan of the system;
program instructions to determine a relationship among the component resources and the data stored on the component resources;
program instructions to receive rules corresponding to retention of record data stored on the component resources of the record retention system;
responsive to receiving a request to delete a user's record data from the record retention system, program instructions to determine a deletion action based on the request to delete the user's record data, the relationship among the component resources, and the rules corresponding to the retention of data on the record retention system;
program instructions to perform the deletion action on the user's record data associated with the request and compliant with the rules corresponding to the retention of the data among the component resources of the record retention system; and
program instructions to record the deletion action and information associated with the deletion action in a deletion log of the record retention system.

13. The computer program product of claim 12, further comprising:
program instructions to receive a notification to perform a restoration of record data of a first timeframe from a backup data component of the component resources of the record retention system associated with the first timeframe;
program instructions to generate a copy of a live record data component of the component resources of the record retention system;
program instructions to apply backup data from the backup data component associated with the first timeframe to the copy of the live record data component;
program instructions to apply the deletion action and the information associated with the deletion action to the copy of the live record data component, based on the deletion log of the record retention system;
program instructions to install the copy of the live record data component of the record retention system as the live record data component of the record retention system; and
program instructions to record the deletion actions in an audit log of the record retention system.

14. The computer program product of claim 12, wherein the rules corresponding to the retention of data stored on the component resources and the deletion actions and information associated with the deletion actions, included in the deletion log, are stored on an immutable device.

15. The computer program product of claim 14, wherein the immutable device is a blockchain structure hosted on a computing device as a component resource of the record retention system.

16. The computer program product of claim 12, wherein, the deletion action includes a soft delete by marking the record data requested for deletion by the user with a "delete" label enabling exclusion of the user's record data from view or query results.

17. A computer system for processing record deletion requests within a record retention system of a distributed cloud environment, the computer system comprising:
one or more computer processors;
one or more computer readable storage media; and
program instructions stored on the one or more computer readable storage media, the program instructions comprising:
program instructions to identify component resources and data of a record retention system by performing a scan of the system;
program instructions to determine a relationship among the component resources and the data stored on the component resources;
program instructions to receive rules corresponding to retention of record data stored on the component resources of the record retention system;
responsive to receiving a request to delete a user's record data from the record retention system, program instructions to determine a deletion action based on the request to delete the user's record data, the relationship among the component resources, and the rules corresponding to the retention of data on the record retention system;

program instructions to perform the deletion action on the user's record data associated with the request and compliant with the rules corresponding to the retention of the data among the component resources of the record retention system; and program instructions to record the deletion action and information associated with the deletion action in a deletion log of the record retention system.

18. The computer system of claim 17, wherein the deletion action removes the record data requested for deletion by the user from the component resources of the record retention system, and maintains compliance of the rules corresponding to retention of record data by retaining the record data requested for deletion by the user in at least one resource of the component resources of the record retention system.

19. The computer system of claim 17, wherein a resource of the component resources of the record retention system is an archive record resource.

20. The computer system of claim 17, further comprising:
program instructions to receive a notification to perform a restoration of record data of a first timeframe of a live record data component of the record retention system to which soft deletions have been applied as deletion actions, wherein soft deleted record data is excluded from view or query results and the soft deleted record data remains in the respective record data component of the record retention system;

program instructions to generate a copy of the live record data component of the record retention system;

program instructions to apply backup data from a backup data component to the copy of the live record data component;

program instructions to apply instances of the soft deletions from a copy of backup data from the backup data component, generated from a most recent timeframe, to the copy of the live record data component of the record retention system;

program instructions to install the copy of the live record data component of the record retention system as the live data component of the record retention system; and program instructions to record the deletion actions in an audit log of the record retention system.

* * * * *